(12) United States Patent  (10) Patent No.: US 8,444,679 B2
Ralph et al.  (45) Date of Patent: *May 21, 2013

(54) CLAVICLE PLATE AND SCREWS

(75) Inventors: James D. Ralph, Bethlehem, PA (US);
Thomas N. Troxell, Pottstown, PA (US);
Mark Michels, Glen Mills, PA (US);
Thomas D. Meade, Allentown, PA (US)

(73) Assignee: MBD Medical LLC, Englewood, NJ (US)

( * ) Notice: Subject to any disclaimer, the term of this patent is extended or adjusted under 35 U.S.C. 154(b) by 228 days.

This patent is subject to a terminal disclaimer.

(21) Appl. No.: 12/422,533

(22) Filed: Apr. 13, 2009

(65) Prior Publication Data

US 2010/0131013 A1  May 27, 2010

Related U.S. Application Data

(63) Continuation-in-part of application No. 12/276,544, filed on Nov. 24, 2008, now Pat. No. 8,403,966.

(51) Int. Cl.
*A61B 17/80* (2006.01)
(52) U.S. Cl.
USPC ............ 606/286; 606/280; 606/283; 606/284
(58) Field of Classification Search
USPC ............................... 606/902, 280–299, 70, 71
See application file for complete search history.

(56) References Cited

U.S. PATENT DOCUMENTS

| | | | |
|---|---|---|---|
| 1,105,105 A | 7/1914 | Sherman | |
| 4,175,555 A | 11/1979 | Herbert | |
| 4,683,878 A * | 8/1987 | Carter | 606/97 |
| 5,558,674 A * | 9/1996 | Heggeness et al. | 606/278 |
| 5,611,354 A * | 3/1997 | Alleyne | 128/846 |
| 5,772,662 A * | 6/1998 | Chapman et al. | 606/281 |
| 5,785,712 A | 7/1998 | Runciman et al. | |
| 5,853,413 A * | 12/1998 | Carter et al. | 606/281 |
| 6,001,099 A * | 12/1999 | Huebner | 606/281 |
| 6,221,073 B1 * | 4/2001 | Weiss et al. | 606/60 |
| 6,506,191 B1 | 1/2003 | Joos | |
| 2002/0165545 A1 * | 11/2002 | Happonen et al. | 606/69 |

(Continued)

FOREIGN PATENT DOCUMENTS

| | | |
|---|---|---|
| FR | 2405706 | 5/1979 |
| JP | 58-83954 | 5/1983 |

OTHER PUBLICATIONS

U.S. Appl. No. 12/276,544—Requirement for Restriction/Election dated Feb. 2, 2011.

(Continued)

*Primary Examiner* — Nicholas Woodall
*Assistant Examiner* — Melissa A Hall
(74) *Attorney, Agent, or Firm* — Lowenstein Sandler LLP

(57) ABSTRACT

A bone plate and system is provided. The bone fixation plate conforms to the contour of an irregularly shaped bone and eliminates the need for pre-bending or intraoperative bending of the plate. The bone plate is applied to the bone in a generally flat condition and the process of installing and tightening the bone screws in the prescribed order serves to contour the plate to the plate to the underlying bone while providing sufficient strength to effect bone healing. The geometry of the plate allows the plate to follow the contour of an irregularly shaped bone, preventing prominence and patient palpability and streamlining the surgical procedure.

16 Claims, 18 Drawing Sheets

U.S. PATENT DOCUMENTS

| | | | |
|---|---|---|---|
| 2003/0195624 A1* | 10/2003 | Muhanna et al. | 623/13.14 |
| 2004/0116930 A1* | 6/2004 | O'Driscoll et al. | 606/69 |
| 2005/0090825 A1* | 4/2005 | Pfefferle et al. | 606/69 |
| 2005/0192578 A1* | 9/2005 | Horst | 606/69 |
| 2007/0276383 A1 | 11/2007 | Rayhack | |

OTHER PUBLICATIONS

U.S. Appl. No. 12/276,544—Response to Election/Restriction dated Apr. 4, 2011.
U.S. Appl. No. 12/276,544—Non-Final Rejection dated Apr. 15, 2011.
U.S. Appl. No. 12/276,544—Response/Amendment dated Jul. 15, 2011.
U.S. Appl. No. 12/276,544—Final Rejection dated Sep. 14, 2011.
U.S. Appl. No. 12/276,544—Response/Amendment dated Nov. 10, 2011.
U.S. Appl. No. 12/276,544—Advisory Action dated Dec. 13, 2011.
U.S. Appl. No. 12/276,544—Request for Continued Examination dated Dec. 14, 2011.
U.S. Appl. No. 12/276,544—Non-Final Rejection dated Jan. 4, 2012.
U.S. Appl. No. 12/276,544—Response/Amendment dated Apr. 2, 2012.
U.S. Appl. No. 12/276,544—Final Rejection dated Apr. 25, 2012.
U.S. Appl. No. 12/276,544—Response/Amendment dated Jul. 19, 2012.

* cited by examiner

CLAVICLE PLATE AND SCREWS

CROSS REFERENCE TO RELATED APPLICATION

This application is a continuation-in-part of U.S. patent application Ser. No. 12/276,544, filed Nov. 24, 2008, now U.S. Pat. No. 8,403,966, the entirety of which is hereby incorporated by reference into this application.

BACKGROUND OF THE INVENTION

1. Field of the Invention

The invention relates to bone plates. More particular, the invention relates to bone plates and accompanying screws for repairing irregularly shaped bones such as the clavicle.

2. Description of the Related Art

Clavicle fractures account for approximately 2-5% of all fractures in the U.S. The majority of these clavicle fractures (approximately 75%) are located in the middle third of the clavicle, a very small percentage (<5%) in the medial third and the remainder in the lateral (or distal) third of the clavicle. Clavicle fractures have traditionally been treated non-operatively, even when one the fragments is substantially displaced. Clavicular nonunion was thought to be rare and of no clinical significance. Recent studies of displaced midshaft fractures of the clavicle, however, have shown a nonunion rate of 15% as well as a 31% unsatisfactory patient-oriented outcome. These statistics were published recently in the study entitled Nonoperative *Treatment Compared with Plate Fixation of Displaced Midshaft Clavicular Fractures. A Multicenter, Randomized Clinical Trial* in *The Journal of Bone and Joint Surgery* (JBJS) in January of 2007. The results of the study illustrate that primary fixation using plates is the recommended course of action for displaced midshaft clavicular fractures in adult patients.

Another type of clavicle fracture requiring plating occurs when the clavicle is not only broken and displaced but when a second fracture occurs causing a completely separated fragment. This condition causes even greater displacement and more patient discomfort and deformity if treated by non-operative procedures.

The clavicle is an irregularly shaped bone that provides the skeletal support for the shoulder. An intact clavicle forces the shoulder outward and backward. When the clavicle is fractured, muscle and soft tissue forces are now unopposed and this often results in the ends of the clavicle displacing (or telescoping inwardly) and rotating relative to one another as the shoulder drops and rotates forward. These forces make it difficult to realign (or reduce) a fractured clavicle so that a bone plate can be properly applied. The surgeon must pull the ends apart and rotate them back into position and must maintain this reduction while the plate is being secured.

The complex shape of the clavicle makes it difficult for a surgeon to bend a flat plate in surgery to match the many contours of the bone. The relative prominence of the clavicle however, requires that an implanted plate have as low a profile as possible, particularly on the ends where it transitions to the bone.

Most of the orthopedic plates and screws that have been approved for use in clavicle repair utilize plates designed for use in other areas of the body and on other bones which have a more uniform shape such as typical long bones. The typical long bone is characterized as being longer than it is wide, having a central shaft and two bulky ends and an inner medullary cavity. Bones of the leg, arm, hand and foot are the classic examples of long bones. These bones have a generally cylindrical shaft with far less curvature than would be found on a clavicle or a mandible. Plates designed for a typical long bone do not fit the more complex contours of the clavicle bone and present a number of problems in fixing the plate to the bone in an acceptable manner. Many of these plates are difficult to bend in general and are particularly difficult to bend at the ends of the plate—exactly where precise adaptation to the clavicle is desired. The shape of the clavicle requires the ends of a flat plate to bend and twist in three dimensions for accurate adaptation to the bone surface. The difficulty in doing so with a traditional long bone plate requires an unwanted expenditure of time and effort in the operating room particularly in light of the difficulty of reducing a displaced clavicle and maintaining that reduction.

A plate has been designed specifically for the clavicle. It is precurved in an "S" shape when viewed from above. While this precurvature generally mimics the profile of the clavicle, studies show that the variability in clavicles results in an inaccurate fit on clavicles in more than half the cases. Moreover, the study only examined two dimensions and did not account for the curvature and twist of the clavicle surface in the third dimension. The prior art S-shaped clavicle plate is flat in the third dimension and the plate is extremely thick making it very hard to bend in order to have the ends follow the surface of the clavicle.

Prior art bone plate designs suited for typical long bones include Huebner (U.S. Pat. No. 6,001,099), which teaches a bone plate with varying rigidity designed to prevent refracture of a bone adjacent to the end of the plate. The plate has essentially uniform thickness over the entire length, with a continuous curvature of the underside that relies upon the combination of varying width and spacing between plate holes to produce the desired reduction in stiffness as one moves from medial to lateral on the plate. Huebner teaches that such plates are particularly adapted to long bones such as those found in the leg, arm hand and foot. The cross-section of his plate is quite similar to that of Sherman (U.S. Pat. No. 1,105,105) in that it has the "concavo-convex cross section" which produces an increase in strength and stiffness over a generally rectangular cross section of the same width and thickness. While this may be applicable to typical long bones with a generally cylindrical shaft, the plate does not provide the needed three-dimensional contourability at its ends nor the reduced profile necessary for a complex and irregular bone such as a clavicle or a mandible.

SUMMARY OF THE INVENTION

A bone plate and system is provided. The bone plate and system are particularly adapted to irregularly shaped bones such as the clavicle and the mandible. The fixation plate conforms to the contour of an irregularly shaped bone and eliminates the need for pre-bending or intraoperative bending of the plate. The bone plate is applied to the bone in a generally flat condition and the process of installing and tightening the bone screws in the prescribed order serves to contour the plate to the underlying bone while providing sufficient strength to effect bone healing. The plate profile and flexibility reduce patient palpability, particularly at the ends of the plate which are often the most critical.

The geometry of the plate allows the plate to follow the contour of an irregularly shaped bone, preventing prominence and patient palpability and streamlining the surgical procedure. The fragment screws allow the plate to be placed in closer contact with the bone than screws presently being used and the smaller profile of the fragment screws permits easier placement of the bone screws adjacent to the fracture.

The system will provide a safe method of repairing discontinuities in a bone with complex curvature.

The bone plating system includes two or three types of implantable devices: a bone fixation plate; bone screws; and, fragment screws. The fragment screws (lag screws) are designed to prevent the plate from sitting on the head of the fragment screw thereby reducing the profile. The bone screws have an aggressive thread profile that allows the screw to firmly engage the bone and provide the compressive force necessary to bend the plate to the bone and provide secure postoperative fixation.

The bone fixation plate has two ends positioned on opposing sides of the plate. A midsection is disposed between the two ends. The plate has a bottom surface and top surface extending from one of the two ends of the plate to the second end. The plate contains one or more holes extending through the plate from the top surface to the bottom. The plate is rigid or stiffer (i.e. less flexible) towards the center of the plate and more flexible as the plate extends toward the ends. This difference in strength/flexibility along the length of the plate can be achieved through a number of different structural configurations. The main consideration in the design of the plate is that it be strong enough near the center to secure the fracture or discontinuous bone and flexible enough near the ends to conform (bend) to the shape of the bones being plated.

The holes of the plate are shaped on the top surface and sized to receive bone screws. The shaped relief at the top of the plate holes allows a fully inserted bone screw to sit in a generally flush relationship with the top of the plate. The two ends of the plate are substantially flat on the bottom surfaces and tapered in thickness. The ends may also be tapered in width so that the width at the ends of the plate is less than at the center of the plate. In one embodiment, the bottom surface of the plate is relieved in the midsection of the plate and the ends of the plate are preferably scalloped on the edges around the holes.

A method for plating a fractured or otherwise discontinuous bone is also described. The method includes utilizing the fixation plate and screws as described herein. The method includes the steps of aligning the discontinuous bone segments, optionally inserting a fragment screw through one segment into the corresponding segment, positioning a bone plate on the aligned bone segments so that the plate extends across the fracture or fractures, driving a bone screw into the bone through a hole closest to the discontinuity, driving in a second bone screw into the bone through a second hole closest to the discontinuity on the opposite side of the discontinuity from the first bone screw. Screws are then driven in the bone through the remaining holes working from the center to the ends of the plate.

In one embodiment, a plate for irregularly shaped bones is described. The plate has two ends positioned on opposing sides of the plate, a midsection disposed between the two ends, and two or more holes extending through the plate and designed to receive bone screws. The two ends have a different underside profile than the midsection of the plate, and the two ends are thinner than the midsection of the plate.

DESCRIPTION OF THE PREFERRED EMBODIMENTS

Overview

A bone fixation plate, a bone plating system, and method of plating a discontinuous bone of irregular shape are disclosed. The bone plating system includes two types of implantable devices: a bone fixation plate and bone screws. Optionally the system includes a third type of implantable device: fragment screws. As used herein, any reference to plate means bone fixation plate unless otherwise noted. Also as used herein any reference to screws includes both bone screws and fragment screws unless otherwise noted. The plate and screws of the plating system are especially suitable for midshaft displaced clavicle fractures. A midshaft displaced clavicle fracture is a fracture that occurs in the middle of the clavicle and one of the bone segments is displaced, the two bony ends generally being offset side-to-side and telescoped end-to-end. This also includes a fracture where there are more than two segments and one segment may be floating.

In operation the bone plating system is applied as follows. The structure of the plate and screws are described in more detail below. After exposing the bone, the bone segments are reduced (aligned) using bone reduction forceps. A fragment or lag screw or screws may optionally be used to secure any bone fragments together prior to plating. The decision to use fragment screws depends on a number of factors including the severity of the fracture but generally, that determination is made by the surgeon at the time of plating. A fragment screw is applied by inserting (or hereafter alternately referred to as driving) a fragment screw through one segment into the other segment. The fragment screw, as described in more detail below, is similar to a lag screw. The distal end threads into the far segment of bone and has clearance in the proximal bone piece. As the tapered end of the screw enters the proximal segment, the two bone segments are drawn together and the tapered thread taps into the proximal bone. With only one break, the surgeon may elect not to use a fragment screw and use only a plate and bone screws.

After the fracture is reduced, the surgeon selects the appropriate sized plate and places a bone screw in one of the holes closest to the fracture and drives the screw into the bone segment. A second screw is placed on the opposite side of the fracture in the closest hole to the fracture. Screws are then placed in the remaining holes and driven into the bone working from the center to the ends of the plate. As these subsequent lateral screws are placed and tightened, the bone plate ends bend and twist as necessary to meet the irregular curvature of the underlying bone.

Preferred Embodiments

Figure 1:
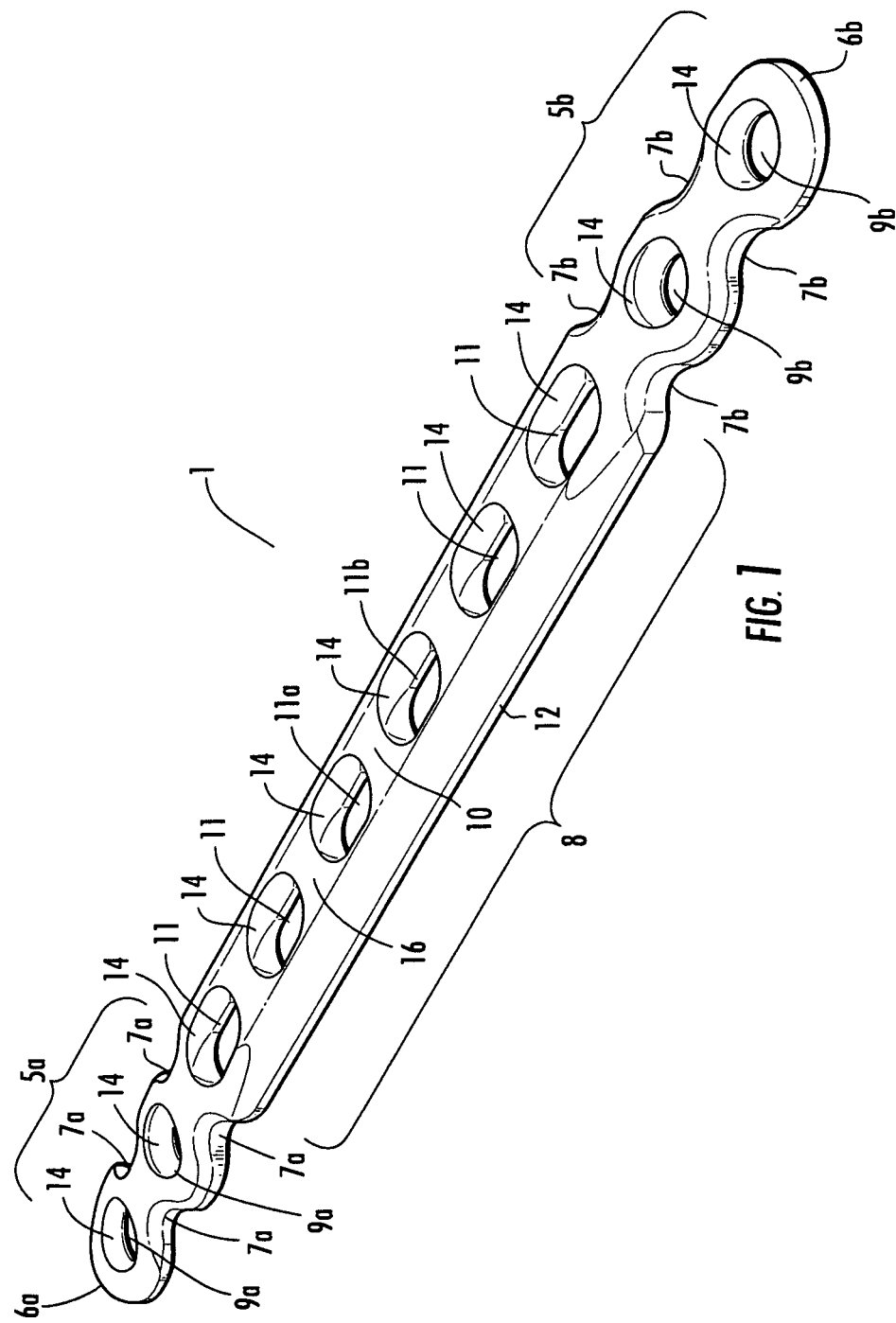
FIG. 1 is a top perspective view of a bone plate in accordance with an embodiment of the invention.
Figure 2:
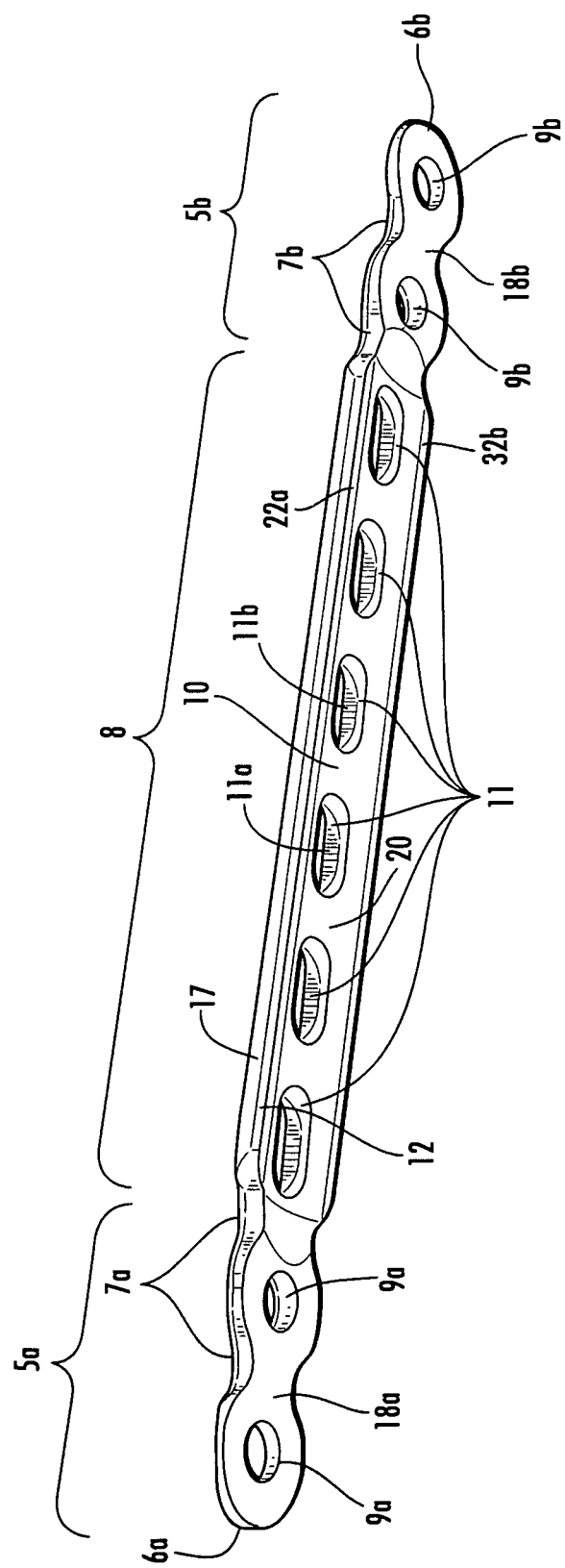
FIG. 2 is a is a bottom perspective view of a bone plate in accordance with an embodiment of the invention

Referring to FIGS. 1-3, a bone fixation plate 1 (alternatively referred to as bone plate or plate) in an embodiment of the invention is shown. As shown in FIG. 1, the bone fixation plate 1 has two ends 5a and 5b and a midsection 8 positioned between the two ends 5*a* and 5*b*. The plate shown in this embodiment has ten holes. However, the number of holes can be varied depending on the length of the plate. Preferably, the number of holes ranges from six holes to at least ten holes.

End holes 9*a* and 9*b*, typically one or two on each end depending on the length of the plate, are round. Midsection holes 11 are preferably ovular or slotted to allow more variability in screw placement and angulation when placing the screws around the fracture area. The number of midsection holes 11 varies, preferably from two to six or more. The midsection holes 11 extend across the length of the midsection 8 of the plate 1. In the embodiment shown in FIGS. 1-2, holes 11*a* and 11*b* are positioned on either side of the approximate center 10 of the plate 1 with the remaining holes spaced approximately evenly apart and extending toward the ends 5*a* and 5*b*. In alternate embodiments, a midsection hole 11 is positioned at or near the center of the plate with the remaining holes approximately evenly spaced towards the ends 5*a* and 5*b* of the plate 1 (See for example FIGS. 5 and 7). FIGS. 4-7 show alternate embodiments of the plate 1 of varying lengths and corresponding varying number of holes. As is shown, the slotted midsection holes 11 are substantially evenly spaced across the length of the midsection 8 of the plate 1 and the ends 5*a* and 5*b* have 1 or 2 round holes, which may have different spacing than the midsection holes.

Preferably all holes, whether round or slotted, are shaped or enlarged where they intersect 14 the top surface 16 of the plate to receive the heads 33 of the bone screws 30 (shown in FIG. 13) and help to reduce the profile of the implants. Preferably, the plate holes 9 and 11 are sized and shaped so that the bone screws 30 are substantially flush with or beneath the top surface 16 (the surface that faces away from the bone when applied) of the bone plate 1.

Figure 3A:
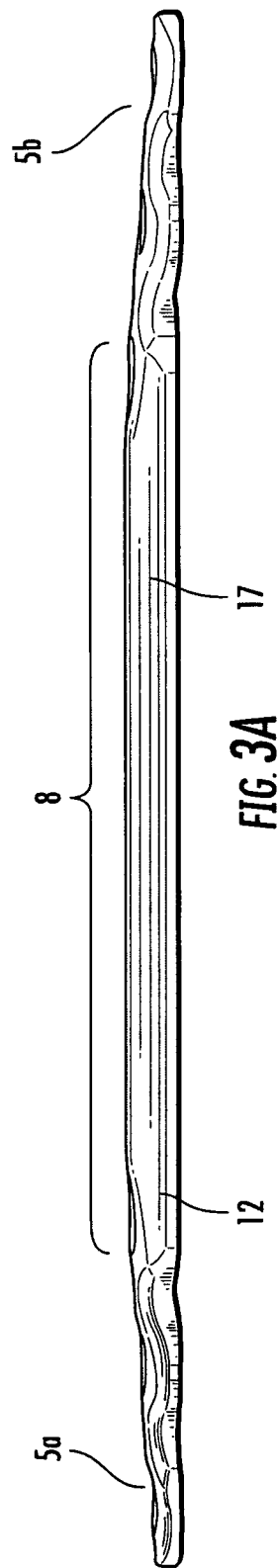
FIG. 3 is a side view of a bone plate in accordance with an embodiment of the invention
Figure 3B:
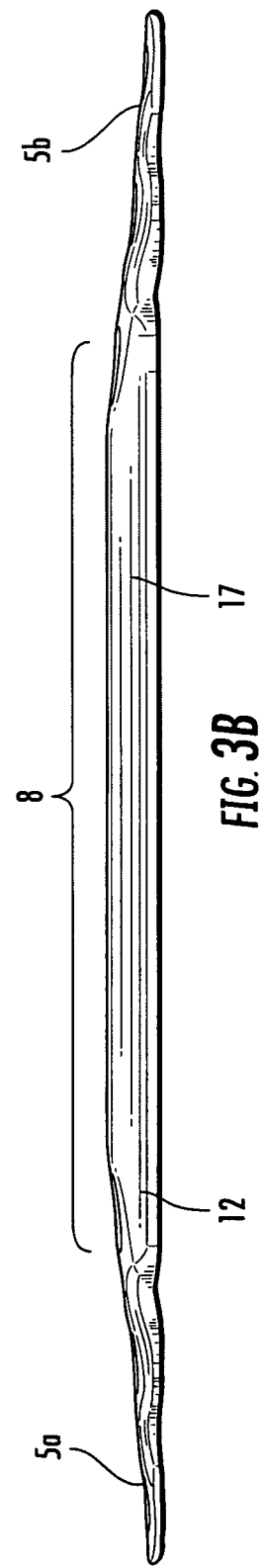
Figure 4:
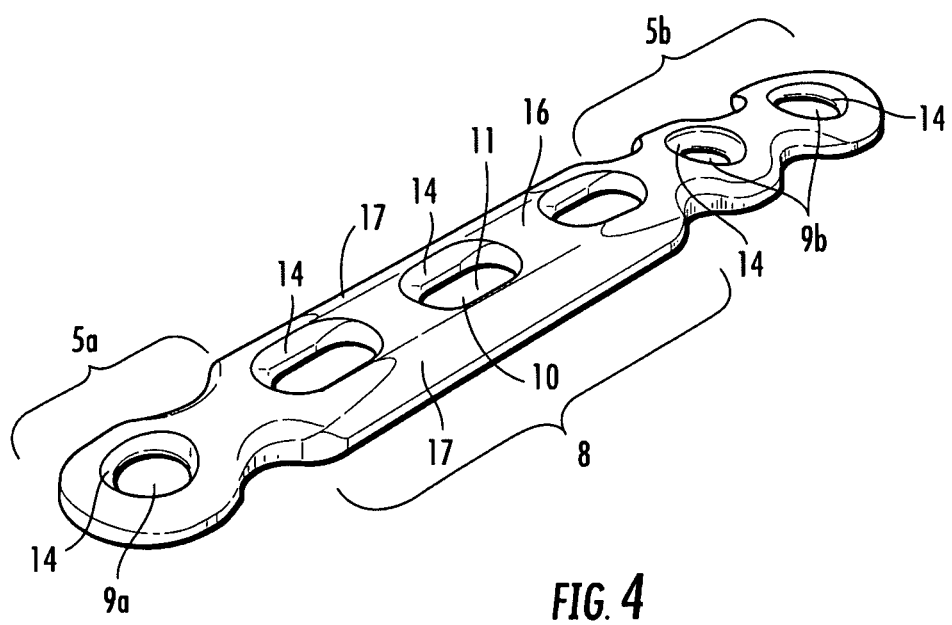
FIGS. 4-7 show a top perspective view of different embodiments of the bone plate of the present invention.
Figure 5:
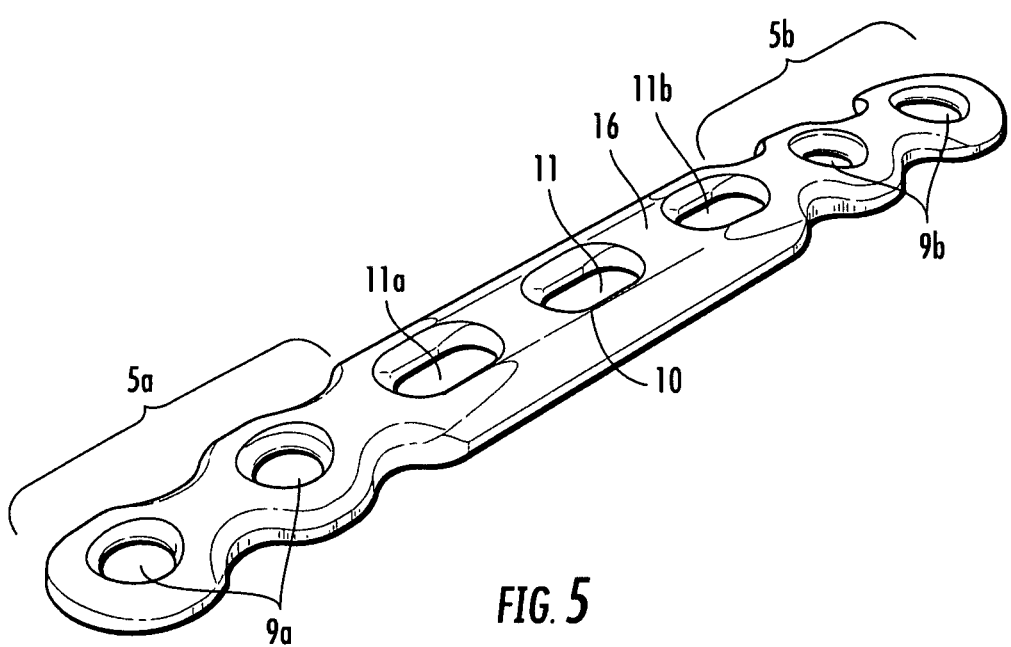
Figure 6:
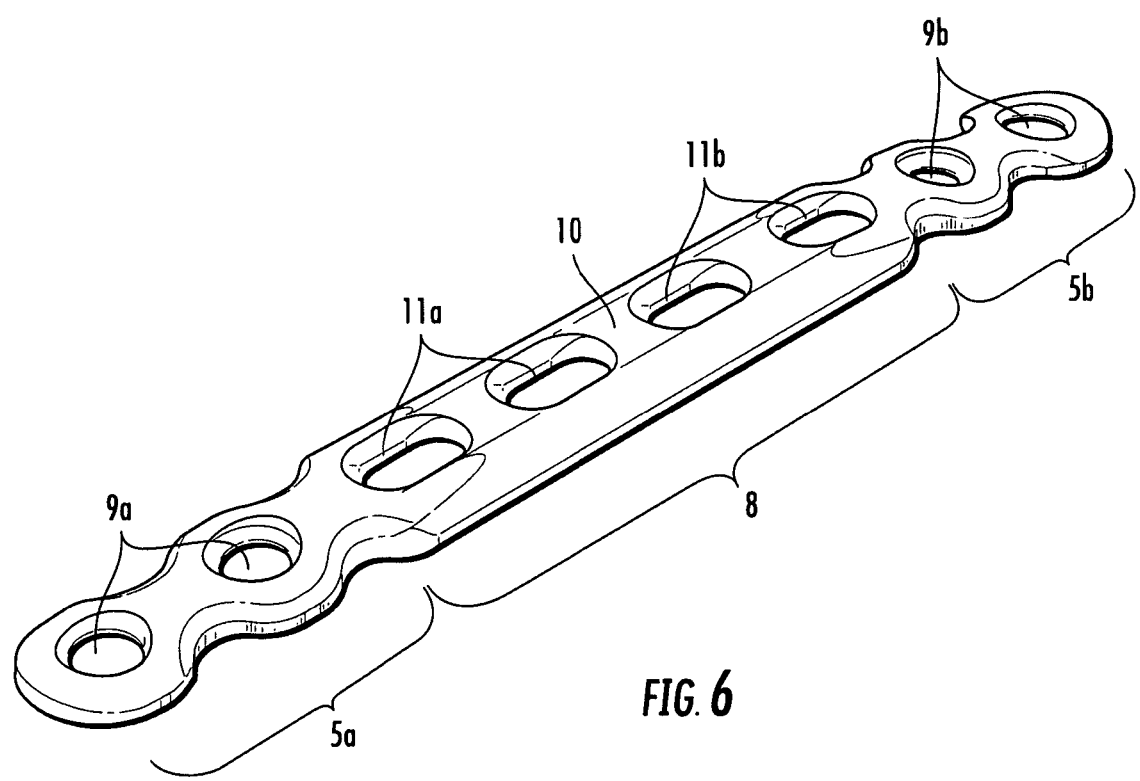
Figure 7:
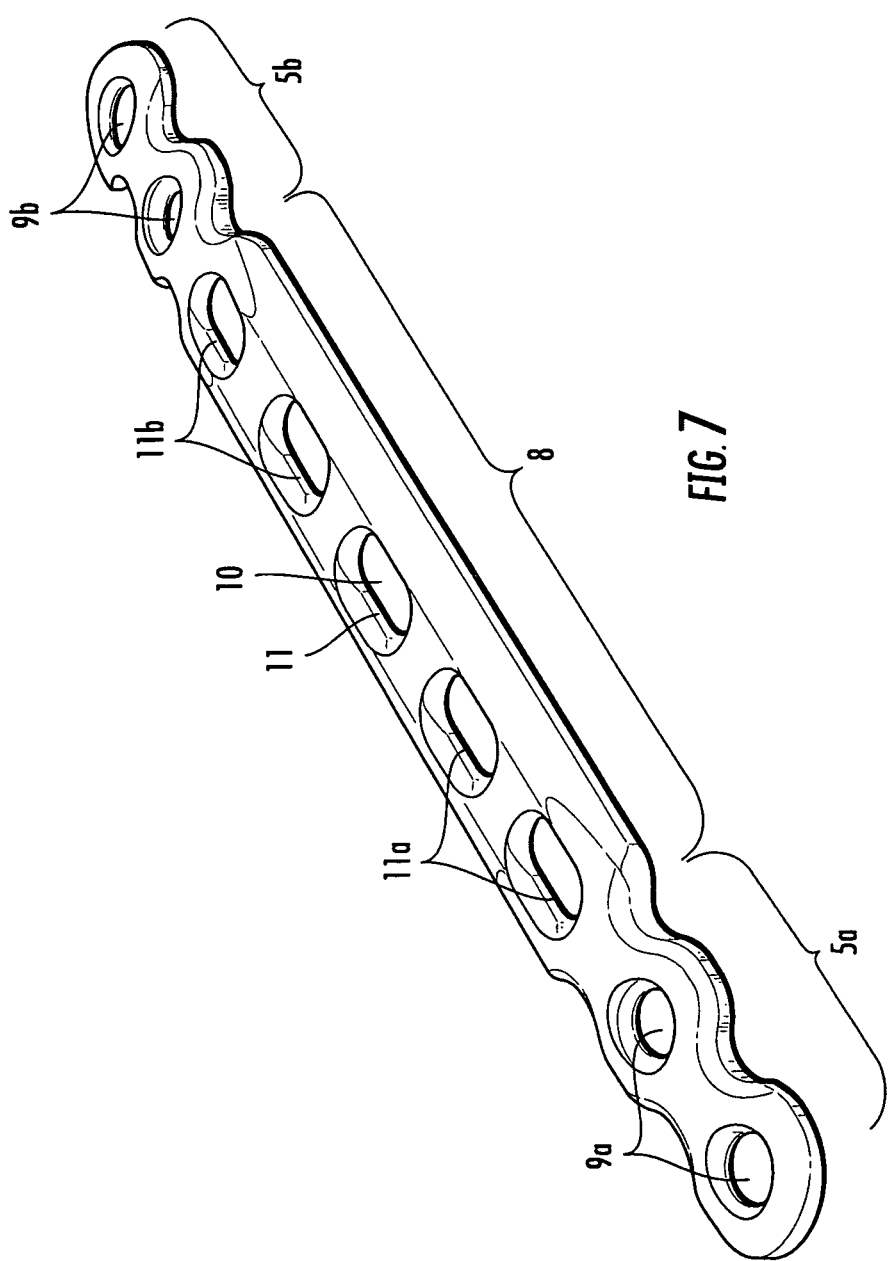

The ends 5*a* and 5*b* are thinner in thickness as compared to the midsection 8. Preferably the ends taper so that the plate gets thinner moving away from the center of the plate. This configuration is best illustrated in FIGS. 3A and 3B which shows the side 12 or edge 12 of the plate. The thickness of the plate 1 decrease as the plate 1 extends toward the ends 5*a* and 5*b*. However, the decrease in thickness can be abrupt so that the center of the plate is one thickness and the ends are a second but smaller thickness. FIG. 3B shows an alternate embodiment with an even more pronounced taper towards the ends of the plate.

As illustrated in FIGS. 1 and 2, plate ends 5*a* and 5*b* are preferably circular or radiused at the outer edge 6*a* and 6*b* of ends 5*a* and 5*b* and scalloped or rounded 7*a* and 7*b* along the edge 12 of the plate 1 around each end hole 9*a* and 9*b*.

As illustrated in FIG. 2, the underside surface 18*a* and 18*b* of the plate 1 is flat at the ends 5*a* and 5*b* in the area of the round holes 9*a* and 9*b*. The underside of the plate 1 has a cylindrical relief 20 in the midsection 8 in the area of the midsection holes 11. The cylindrical relief 20 creates two rails 22*a* and 22*b* at the sides 12 of the plate 1. The rails 22*a* and 22*b* allow the plate 1 to contact the bone better in the area of the fracture than conventional flat plates. This configuration also better enables the plate 1 to be drawn more tightly to the bone (not shown) as the screws (not shown) are tightened.

The configuration of the plate 1, allows the plate to conform to the profile of an irregularly shaped bone, without having to pre-bend the plate to fit to the curvature of the bone and while still providing the necessary rigidity for bone healing. The underside radius on the central section of the plate allows it to sit tightly against the bone and minimize the plate profile. This underside radius also imparts some of the strength advantages but only in a localized area which is designed to span the discontinuity of the bone. FIGS. 8 through 11 show alternate embodiments or configurations that provide the rigid to flexible profile as the plate moves from the center towards the ends. That is, while the embodiments shown in FIGS. 8-11 have different structural features, they are similar in that they are stronger and less flexible in the midsection of the plate and more flexible towards the ends of the plate, which is the most important to the application of the bone plate to the irregular shaped bone and subsequent healing of the bone. The embodiments shown herein are just few configurations that can be used; many configurations are possible that achieve this rigid-to-flexible plate profile. The exact structural configuration to achieve the profile is less important than the presence of the rigid-to-flexible profile along the length of the plate.

When a bone plate 1 is applied to an irregular shaped bone, the screws closest to the discontinuity bear the greatest load. Therefore, the plate bears the greatest load above and directly adjacent to the discontinuity and this load decreases as one moves outward toward the ends of the plate. Toward the ends of the plate 1, strength and stiffness become less important than three-dimensional contourability, particularly on irregularly shaped bones which are not generally cylindrical. For this reason, the underside radius on the central section of the plate transitions into a generally flat underside toward the ends of the plate. This increased three-dimensional flexibility allows the ends of the plate to bend and twist to meet the underlying bone surface and this in situ adaptation of the plate to the bone can be accomplished using only the compressive force of the bone screws.

Figure 8:
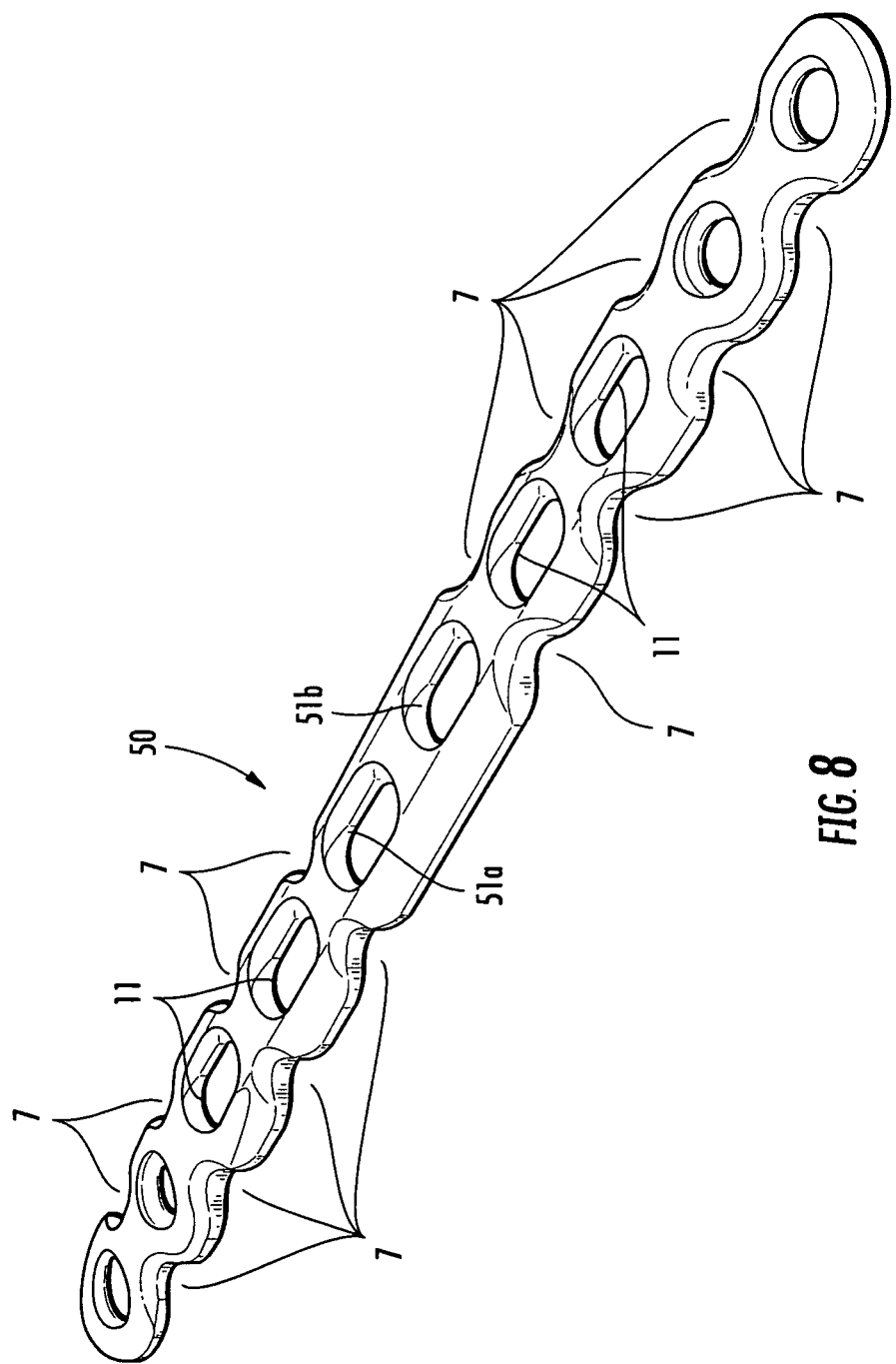
FIGS. 8-12 show alternate embodiments of the bone plate of the present invention.

FIG. 8 illustrates an alternate embodiment of the bone plate. As with the bone plate 1 described above, the configuration of this bone plate allows the plate 50 to conform to the profile of an irregularly shaped bone, without having to pre-bend the plate to fit to the curvature of the bone and while still providing the necessary rigidity for bone healing. In this embodiment, the scallops 7 extend more medially. Plate 50 has similar strength and stiffness between the two center slots or holes 51*a* and 51*b* but exhibits greater flexibility between all other slotted midsection plate holes 11.

Figure 9A:
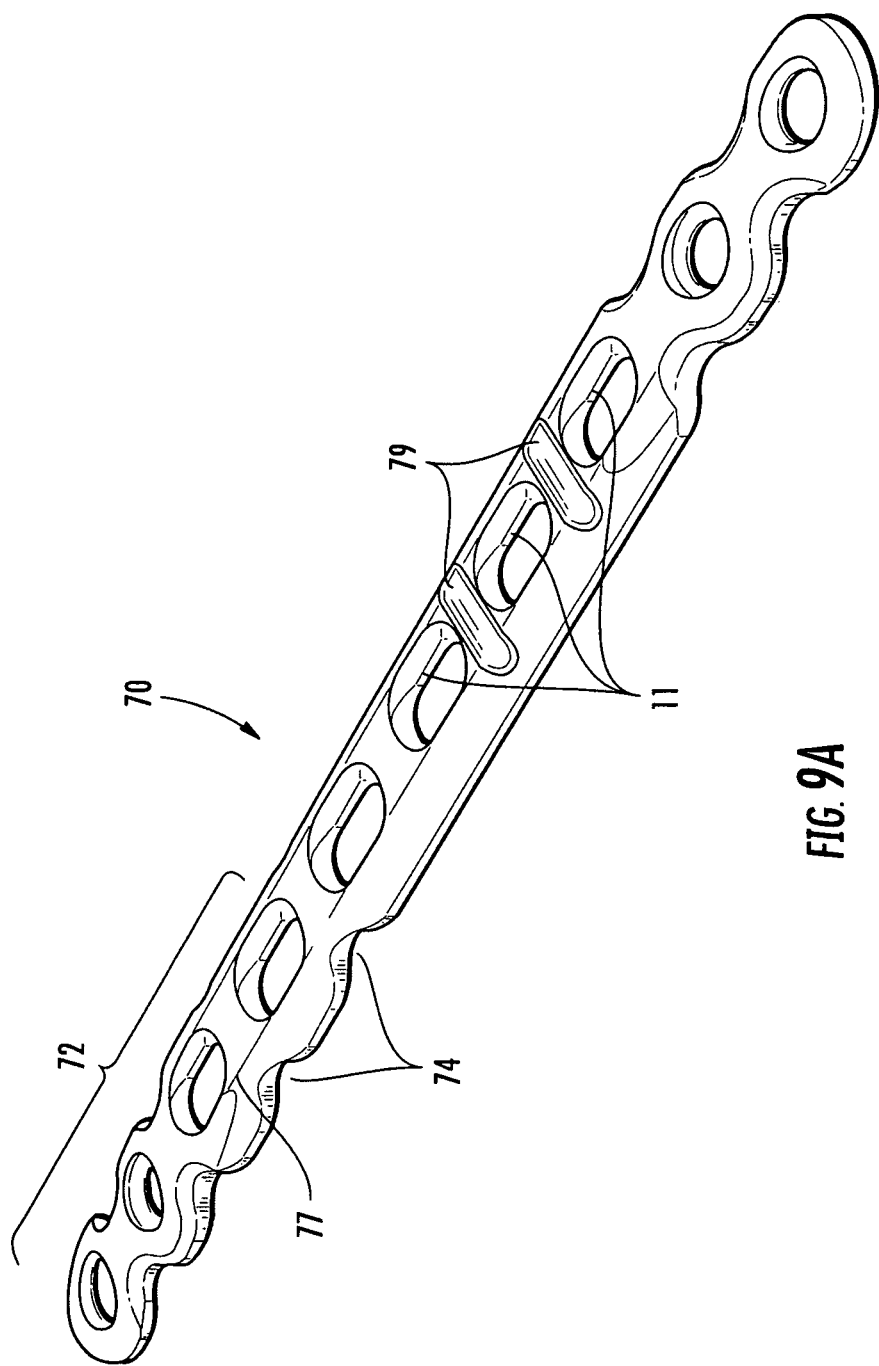
Figure 9B:
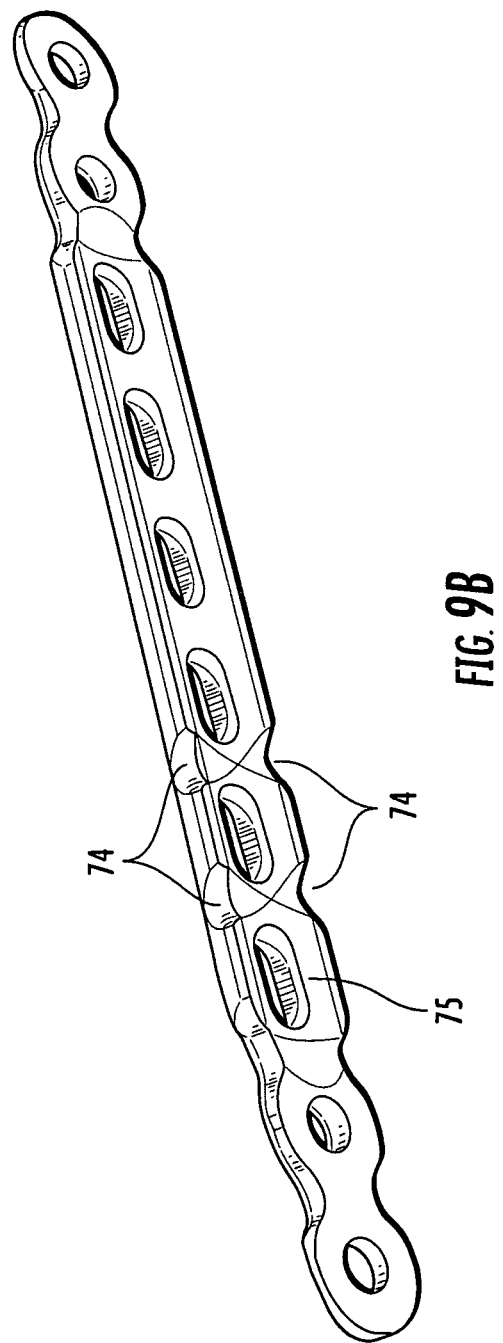

FIGS. 9A and 9B illustrate another alternate embodiment of the bone plate. Plate 70 is an asymmetric bone plate. FIG. 9A shows a top perspective view and FIG. 9B shows a bottom perspective view. One side 72 of the plate 70 has partial or angled scallops 74 positioned between slotted holes 11. These scallops 74 remove more material from the bottom 75 of the plate 70 than the top 77 although this direction of angulation could be reversed to remove more material from the top. The opposite side of the plate has radiused grooves 79 on the top of the plate 70 between the slotted midsection holes 11 on the top 77 of the plate 70. Alternately, the slots can be located on the bottom surface of the plate. Both the angled scallops and the perpendicular grooves decrease the plate cross section between holes thereby increasing the flexibility of the plate in those areas. In the embodiment shown they are positioned on opposite ends of the plate. The exact number and positioning of the scallops and perpendicular grooves could be altered to achieve the desired rigidity/flexibility profile of the plate.

Figure 10A:
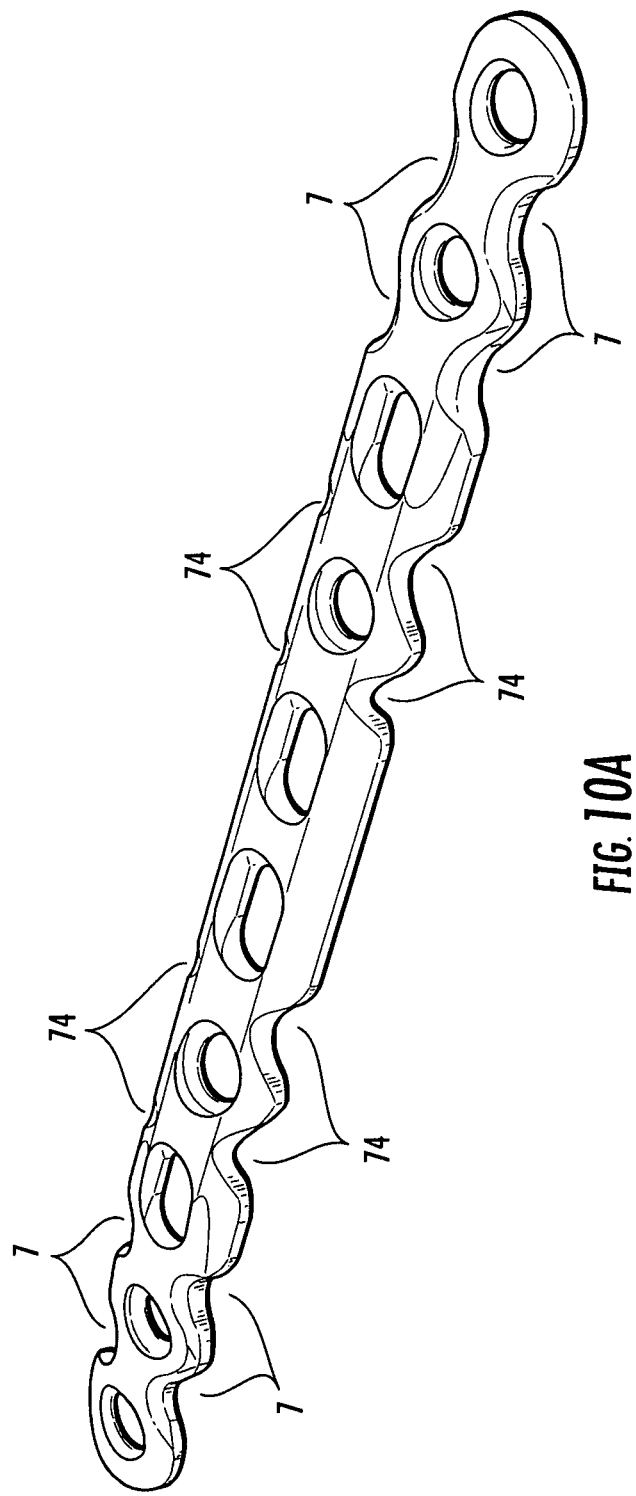
Figure 10B:
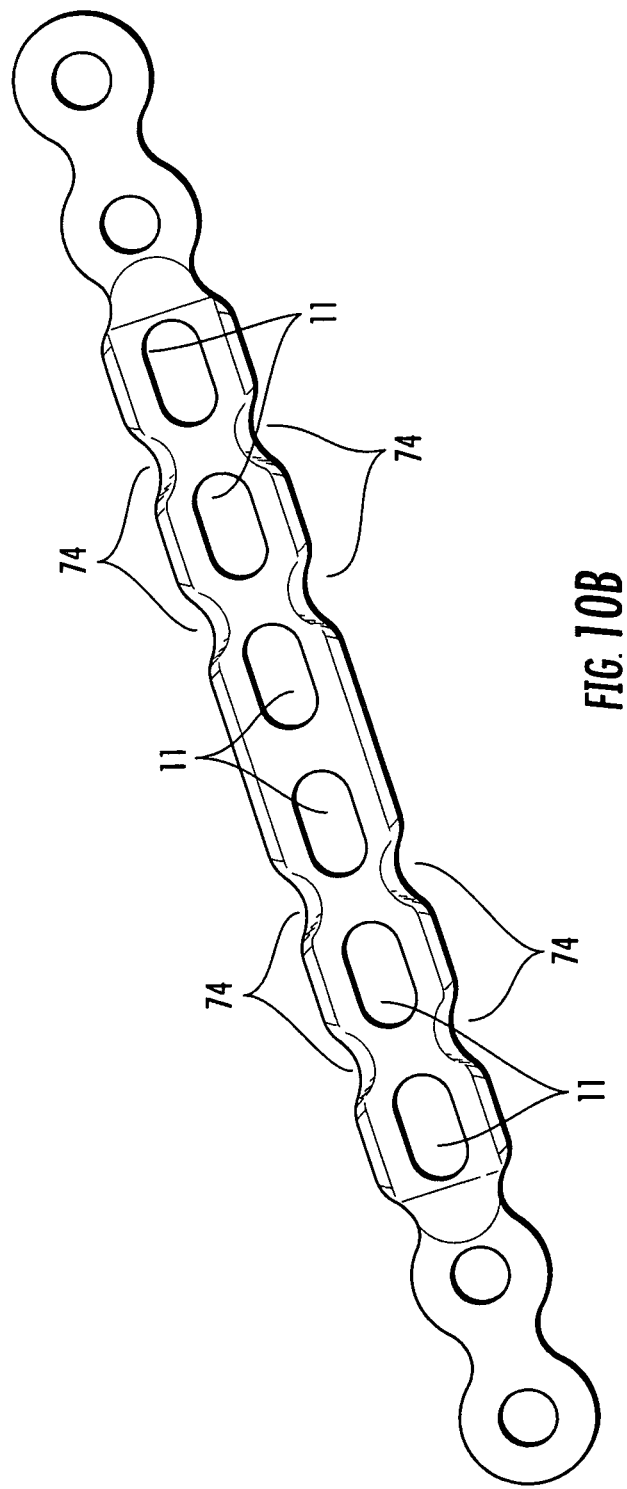

FIGS. 10A and 10B illustrate another alternate embodiment of the bone plate. FIG. 10A shows a top perspective view and FIG. 10B shows a bottom view. In this embodiment the angled scallops 74 are arranged symmetrically on the bone plate. The plate has slotted midsection holes 11 but those holes could also be round.

Figure 11A:
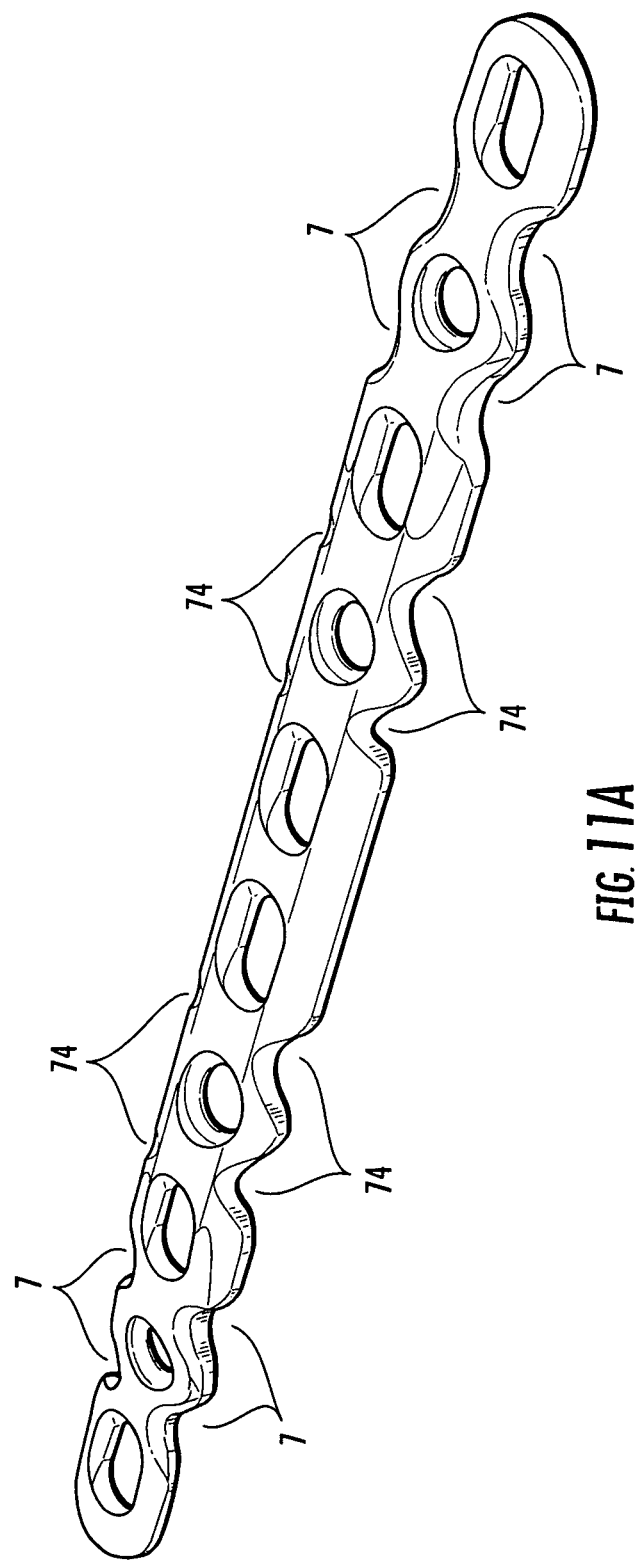
Figure 11B:
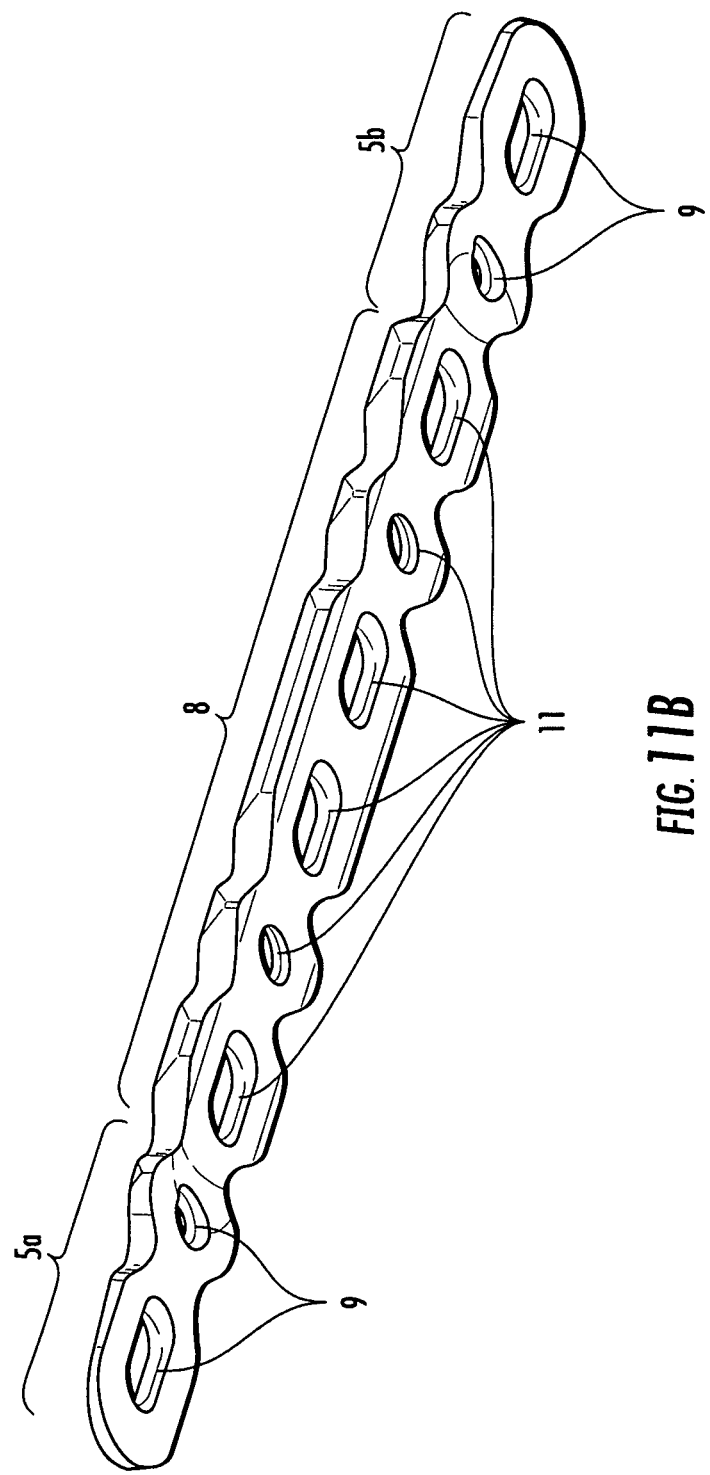

FIGS. 11A and 11B illustrate another alternate embodiment of the bone plate. FIG. 11A shows a top perspective view and FIG. 11B shows a bottom perspective view. In this embodiment, the midsection holes 11 alternate between round shape and slotted shape, while the end holes 9 are slotted. Perpendicular scallops 7 are positioned between all but the two center midsection holes 11'. Again this configuration achieves the function of having increased flexibility towards the end of the plates and increased strength towards the middle.

Figure 12A:
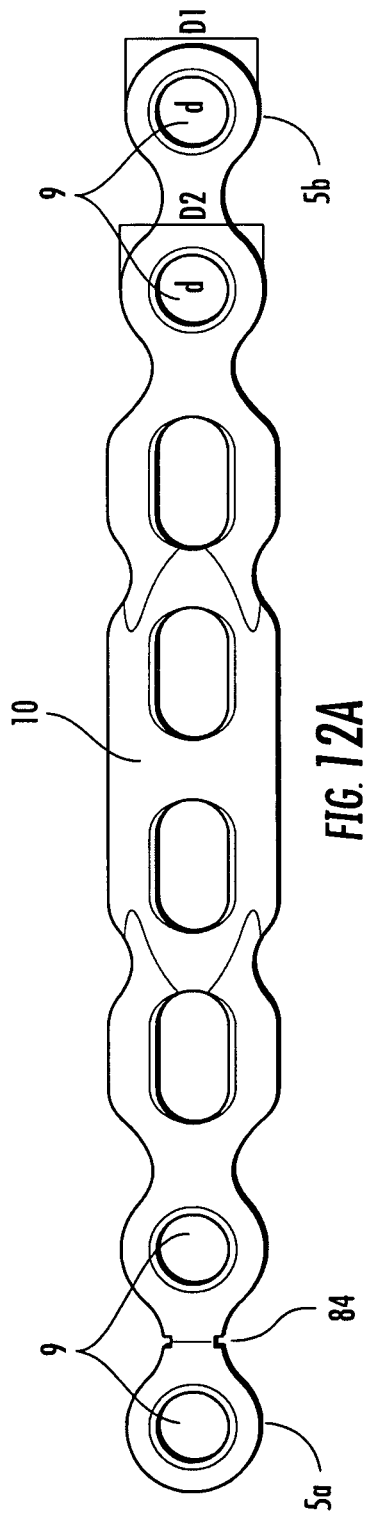
Figure 12B:
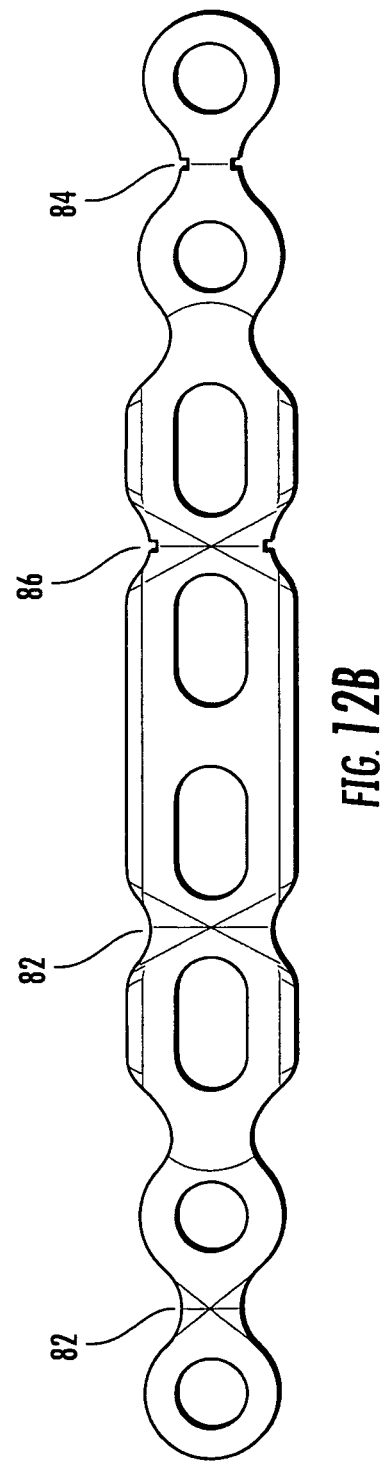

FIGS. 12A and 12B illustrate another alternate embodiment of the bone plate. FIG. 12A shows a top perspective view and FIG. 12B shows a bottom perspective view. In this embodiment, the width of the plate decreases towards the ends 5a and 5b of the plate. In particular, the outer diameter D of the rounded portions are smaller towards the ends of the plate but the diameter or bore, d, of the end holes 9 remain unchanged. In FIG. 12A, D1 is smaller than D2, which is smaller than the width of the plate at the approximate center 10 of the plate.

Figure 13:
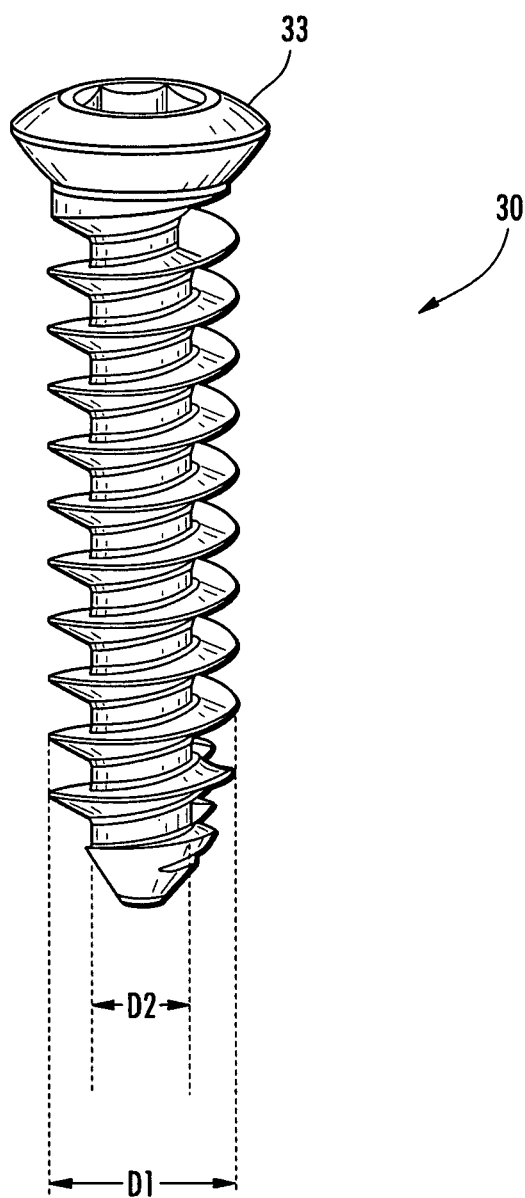
FIG. 13 is a perspective view of a preferred bone screw that can be used to secure the plate to a clavicle.

Again, this structural feature functions to increase the flexibility of the plate towards the ends of the plate. Additional optional features include diamond shaped cross cuts or slits 82 on the bottom side of the plate between the holes. Notches 84 on the outer edges can be included to enhance the flexibility. A combination of both can be used such as illustrated at 86. One plate can have one or both, or any combination of the features described herein to achieve the desired flexibility profile FIG. 13 shows a preferred bone screw 30 that is used to secure the bone plate 1 to a bone. The bone screw 30 is preferably in the diameter range of 2-6 mm and of sufficient length to provide bicortical purchase. Bone screw 30 has a shaped head 33 which fits into the shaped countersink 14 in the plate 1 to produce a generally flush condition when the screw is fully inserted into the plate. The bone screws 30 of the invention have a deep thread with sufficient pitch to allow the screws to bite into the bone and produce the compressive forces necessary to contour the ends or the plate to the underlying bone without the risk of stripping the screws while they are being tightened. Thread depth is measured by the difference between the outside (or major) diameter D1 of a screw and the core (or minor) diameter D2. This can be expressed as a ratio.

$$\text{Major Diameter/Minor Diameter} = \text{Thread Depth Ratio}$$

Typically, bone screws for long bones have a cortical thread form with a shallower thread depth which is sufficient for simply clamping a pre-bent plate to a bone. These typical long bone screws have Thread Depth Ratio in the range of about 1.2 to about 1.5. In many cases, however, this thread depth does not permit sufficient thread engagement to allow these screws to reliably bend a plate of the invention to the bone in situ as described above. In the preferred embodiment of the bone screws 30 used with the bone plate 1 of the invention, the Thread Depth Ratio is in the range of 1.5 to 2.0.

Figure 14:
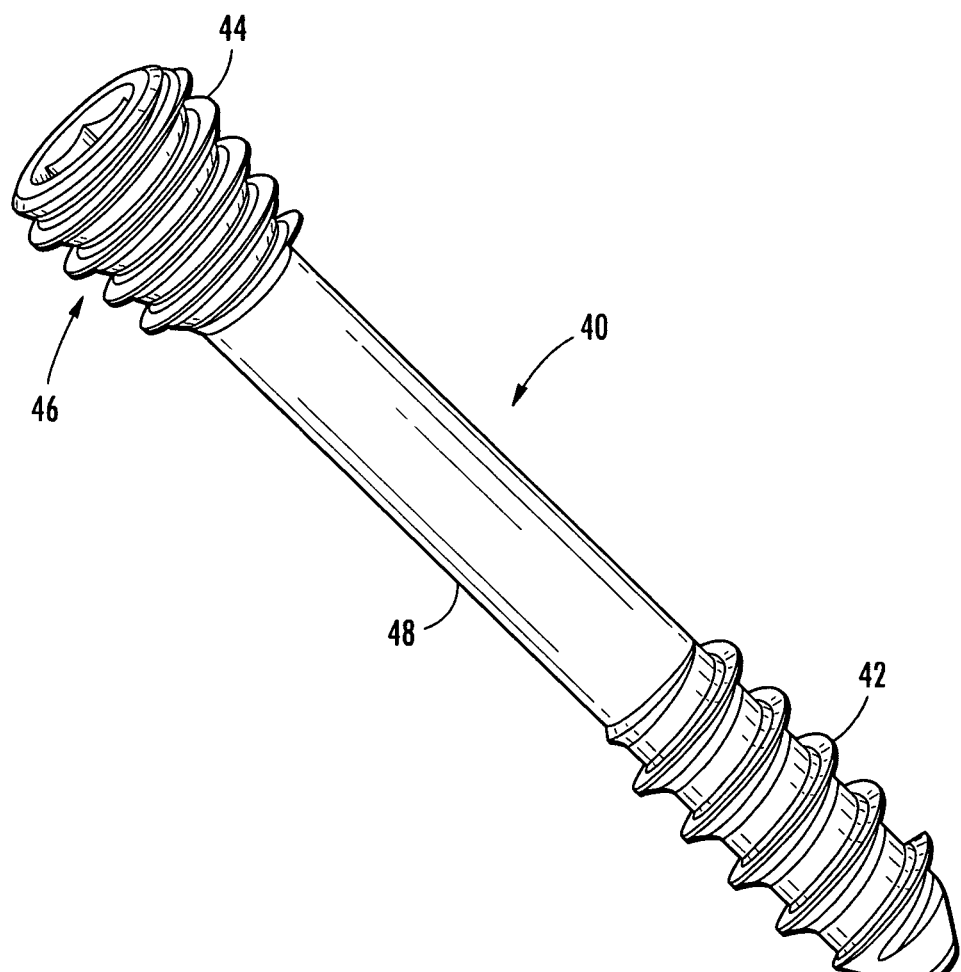
FIG. 14 is a perspective view of a preferred fragment screw.

FIG. 14 shows a preferred fracture screw 40 that may optionally be used prior to plating. Fragment screw 40 is approximately 2.5 mm diameter at the distal threaded end 42 and has a tapered thread 44 at the proximal end 46. Fragment screws may be used in a variety of sizes.

Fragment screw 40 has self tapping threads 42 and 44 that preferably have a Thread Depth Ratio in the range of 1.2 to 2.0. This permits its use for bi-cortical installation. Fragment screw 40 has a reduced diameter in the midshaft area 48 of the screw. This configuration allows the 2 bone fragments to be drawn tightly together. The tapered thread 44 at the proximal end 46 acts as a screw head and draws the fragments together and helps to prevent screw backout.

Additionally, the tapered head 44 gives a smaller profile than a conical head and can be drawn down until it is flush or almost flush with the surface of the bone. This allows the plate 1 to seat more closely to the bone and the smaller size allows the bone screws 30 adjacent to both sides of the fracture to be placed more easily.

Figure 15:
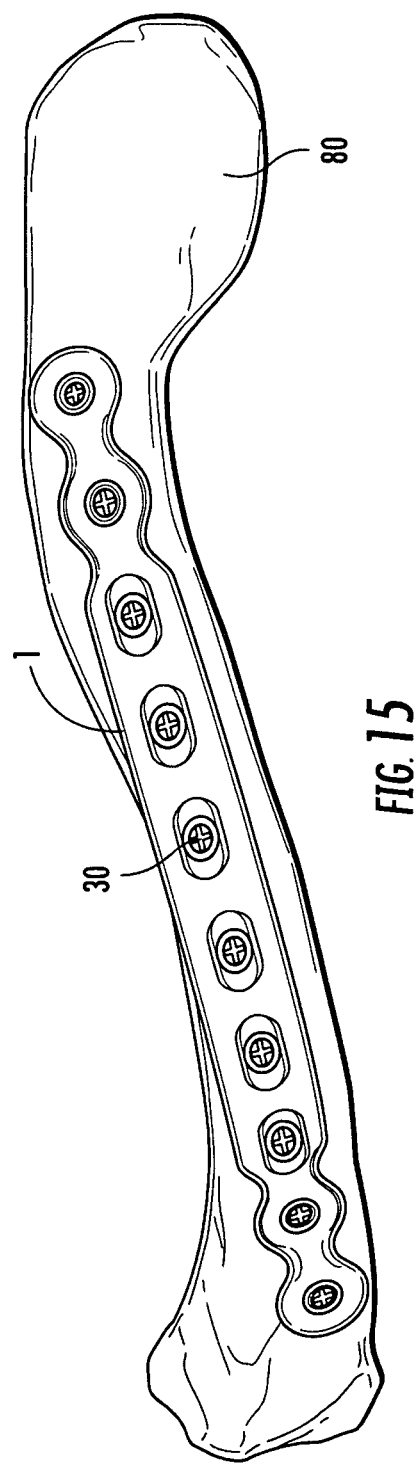
FIG. 15 show a top view of bone plate secured to a clavicle bone.

FIG. 15 shows a plate 1 secured to a clavicle bone 80 with bone screws 30. The plate 1 conforms to the curvature of the bone 80 without any pre-bending of the plate 1 prior to mounting the plate 1 on the bone 80. The heads 33 of the bone screws 30 do not protrude substantially beyond the outward facing surface 16 of the plate 1, thereby providing a very low profile when secured.

The bone plate and its components may be constructed of any suitable biocompatible material known to have sufficient structural strength and durability, such as stainless-steel, alloys, cobalt alloys or titanium alloys, including any suitable ASTM or ISO standard materials as set forth on the United States Food and Drug Administration website, may be used. An exhaustive list is available on the FDA website which also provides the reference numbers and effective dates of the ASTM or ISO standards for many of the materials that are suitable. Some examples include unalloyed titanium, titanium alloyed with aluminum, niobium and/or vanadium, stainless steels and other irons alloyed with molybdenum, chromium, cobalt, tungsten, nickel, manganese in various combinations, various other stainless steels or other iron alloys, for example, with aluminum oxides, zirconium oxides, tantalum and calcium phosphates. Any acceptable polymeric material may be used, such as PEEK (polyetheretherketone), with sufficient flexibility to mimic the micromotion of normal bone, to stimulate bone growth. The PEEK may be combined with other materials or polymers. Also, ceramic filled biocompatible polymers, or other biocompatible materials of sufficient strength to stabilize the bone during healing, or correct a fracture of the bone may be used to make the bone plate, or any component or member of the bone plate. Other materials which may be used include bioabsorbable materials and collagen. One or more materials may be used in building, manufacturing and assembling the bone plates or any component of the bone plates. For example, combinations of the materials discussed herein may be used.

The bone plate or any component or member of the bone plate, may further comprise bioabsorbable drug delivery devices, such as implantable modular drug delivery devices. Examples of bioabsorbable drug delivery devices are described in the co-pending application, U.S. Ser. No. 11/135,256 filed May 23, 2005, IMPLANTABLE PROSTHETIC DEVICES CONTAINING TIMED RELEASE THERAPEUTIC AGENTS, which is incorporated herein in its entirety by reference. Such devices, for example, may be placed within a dedicated bore, such as a drug delivery bore, or within a bone screw bore or locking means bore. Accordingly, the bone plate can be used to deliver drugs, if needed Bioabsorbable surgical fasteners or bone screws made from bioabsorbable materials may be used to apply the bone plate, i.e. to apply the first member and/or second member, to the bone of a patient. For example, the materials described in the co-pending patent application, U.S. Ser. No. 11/025,231, filed Dec. 29, 2004, SURGICAL FASTENERS AND RELATED IMPLANT DEVICES HAVING BIOABSORBABLE COMPONENTS, which is incorporated herein in its entirety by reference, may be used for the bone screws and the bone screws may be the surgical fasteners described in this co-pending patent application.

There will be various modifications, adjustments, and applications of the disclosed invention that will be apparent to those of skill in the art, and the present application is intended to cover such embodiments. Accordingly, while the present invention has been described in the context of certain preferred embodiments, it is intended that the full scope of these be measured by reference to the scope of the following claims.

What is claimed is:

1. A plate for irregularly shaped bones comprising
a top surface and a bottom surface;
two ends positioned on opposing sides of the plate;
a midsection disposed between the two ends, the midsection having a width, a center point and two midsection ends positioned on opposing sides of the center point; and
two or more holes extending through the top surface and bottom surface of the two ends of the plate and designed to receive bone screws;
the plate having a longitudinal axis running through the center of the two or more holes, wherein the longitudinal axis intersects the two ends of the plate; the underside profile of the plate being concave in the midsection in a plane perpendicular to the longitudinal axis and transitioning to a flat surface at each of the two ends; and
the two ends having scalloped edges around the holes, and being thinner and having a diameter that is less than the width of the midsection of the plate to provide increased three-dimensional flexibility at the two ends, thereby allowing the two ends to bend and twist to meet a bone surface using only the compressive force of a bone screw.

2. The bone plate of claim 1 wherein the holes are configured on the top surface to receive the heads of bone screws.

3. The bone plate of claim 1 wherein the bottom surface has slits disposed between the holes.

4. The bone plate of claim 1 wherein the bottom surface has notches disposed between the holes.

5. A plate system for irregularly shaped bones comprising
A bone plate; and
bone screws sized to secure the plate to a bone and to contour the ends of the plate to the curvature of a bone as they are inserted,
Wherein the plate comprises
a top surface and a bottom surface;
two ends positioned on opposing sides of the plate;
a midsection disposed between the two ends, the midsection having a width, a center point and two midsection ends positioned on opposing sides of the center point; and
two or more holes extending through the top surface and bottom surface of the two ends of the plate and designed to receive bone screws;
the plate having a longitudinal axis running through the center of the two or more holes, wherein the longitudinal axis intersects the two ends of the plate; the underside profile of the plate being concave in the midsection in a plane perpendicular to the longitudinal axis and transitioning to a flat surface at each of the two ends; and
the two ends having scalloped edges around the holes, and being thinner and having a diameter that is less than the width of the midsection of the plate to provide increased three-dimensional flexibility at the two ends, thereby allowing the two ends to bend and twist to meet a bone surface using only the compressive force of a bone screw.

6. The bone plate system of claim 5 wherein the plate holes and screw head are sized and shaped so that the top of the screw is substantially flush with the top surface of the plate when the screws are fully inserted into the holes.

7. The bone plate system of claim 5 wherein the bottom surface of the bone plate has slits disposed between the holes.

8. The bone plate system of claim 5 further comprising fragment screws for securing fragments prior to mounting the clavicle.

9. The bone plate system of claim 8 wherein the fragment screw has a reduced diameter in the midshaft area of the screw.

10. The bone plate system of claim 9 wherein the fragment screw has tapered thread at the proximal end.

11. The bone plate system of claim 5 wherein the bottom surface has notches disposed between the holes.

12. A plate for irregularly shaped bones comprising
a top surface and a bottom surface;
two ends positioned on opposing sides of the plate;
a midsection disposed between the two ends, the midsection having a width, a center point and two midsection ends positioned on opposing sides of the center point; and
two or more holes extending through the top surface and bottom surface of the two ends of the plate and designed to receive bone screws;
one or more holes extending through the top surface and bottom surface at each end of the plate;
the plate having a longitudinal axis running through the center of the two or more holes at the midsection of the plate and the one or more holes at each end of the plate, and wherein the longitudinal axis intersects the two ends of the plate;
the underside profile of the plate being concave in the midsection in a plane perpendicular to the longitudinal axis and transitioning to a flat surface at each of the two ends;
one of the midsection ends having a scalloped edge, and the opposite midsection end having a non-scalloped edge; and
the two ends of the plate being thinner and having a diameter that is less than the width of the midsection of the plate to provide increased three-dimensional flexibility at the two ends, thereby allowing the two ends to bend and twist to meet a bone surface using only the compressive force of a bone screw.

13. The plate of claim 12 having scallop edges on the plate around the holes on the ends of the plate.

14. The plate of claim 12 having radiused grooves between the holes on the ends of the plate.

15. The plate of claim 12 wherein the bottom surface of the bone plate has slits disposed between the holes.

16. The plate of claim 12 wherein the bottom surface has notches disposed between the holes.

* * * * *